(12) United States Patent
Gilbert et al.

(10) Patent No.: US 10,842,563 B2
(45) Date of Patent: Nov. 24, 2020

(54) SYSTEM AND METHOD FOR POWER CONTROL OF ELECTROSURGICAL RESONANT INVERTERS

(71) Applicant: COVIDIEN LP, Mansfield, MA (US)

(72) Inventors: James A. Gilbert, Boulder, CO (US);
Joshua H. Johnson, Arvada, CO (US);
Eric J. Larson, Broomfield, CO (US);
Brian L. Roberts, Loveland, CO (US);
Braddon M. Van Slyke, Arvada, CO (US)

(73) Assignee: COVIDIEN LP, Mansfield, MA (US)

( * ) Notice: Subject to any disclaimer, the term of this patent is extended or adjusted under 35 U.S.C. 154(b) by 420 days.

(21) Appl. No.: 14/190,895

(22) Filed: Feb. 26, 2014

(65) Prior Publication Data

US 2014/0276754 A1 Sep. 18, 2014

Related U.S. Application Data

(60) Provisional application No. 61/789,005, filed on Mar. 15, 2013.

(51) Int. Cl.
*A61B 18/12* (2006.01)
*A61B 18/18* (2006.01)
(Continued)

(52) U.S. Cl.
CPC .......... *A61B 18/18* (2013.01); *A61B 18/1206* (2013.01); *A61B 18/1815* (2013.01);
(Continued)

(58) Field of Classification Search
CPC ........... A61B 2018/00648; A61B 2018/00702; A61B 2018/00678; A61B 2018/00726; A61B 2018/1226

See application file for complete search history.

(56) References Cited

U.S. PATENT DOCUMENTS 3,952,748 A * 4/1976 Kaliher .................. A61B 18/12
219/770
4,430,625 A 2/1984 Yokoyama
(Continued)

FOREIGN PATENT DOCUMENTS

CN 1134028 A 10/1996
CN 102460895 A 5/2012
(Continued)

OTHER PUBLICATIONS

Vallfors et al., "Automatically Controlled Bipolar Electrosoagulation-'COA-COMP'", Neurosurgical Review 7:2-3 (1984) pp. 187-190.
(Continued)

*Primary Examiner* — Daniel W Fowler
(74) *Attorney, Agent, or Firm* — Carter, DeLuca & Farrell LLP

(57) ABSTRACT

An electrosurgical generator is disclosed. The generator includes an RF output stage configured to generate at least one electrosurgical waveform including a plurality of cycles; at least one sensor coupled to the RF output stage, the at least one sensor configured to measure a voltage and a current of the at least one electrosurgical waveform; and a controller coupled to the at least one sensor and the RF output stage, the controller including a proportional-integral-derivative controller having at least one of voltage limiter or a current limiter, the proportional-integral-derivative controller configured to saturate the RF output stage based on voltage-current characteristics of the RF output stage.

8 Claims, 14 Drawing Sheets

(51) Int. Cl.
*H02M 7/5387* (2007.01)
*A61B 18/00* (2006.01)
*H02M 7/48* (2007.01)

(52) U.S. Cl.
CPC .............. *H02M 7/53871* (2013.01); *A61B 2018/00678* (2013.01); *A61B 2018/00702* (2013.01); *A61B 2018/00827* (2013.01); *A61B 2018/00892* (2013.01); *A61B 2018/1213* (2013.01); *A61B 2018/1286* (2013.01); *H02M 2007/4815* (2013.01); *Y02B 70/1441* (2013.01)

(56) References Cited

U.S. PATENT DOCUMENTS

| | | | |
|---|---|---|---|
| 4,661,766 A * | 4/1987 | Hoffman | H01H 47/325 |
| | | | 318/139 |
| 4,959,606 A | 9/1990 | Forge | |
| 5,249,121 A | 9/1993 | Baum et al. | |
| 5,318,563 A | 6/1994 | Malis et al. | |
| 5,396,194 A | 3/1995 | Williamson et al. | |
| 5,559,688 A | 9/1996 | Pringle | |
| 5,596,466 A | 1/1997 | Ochi | |
| 5,694,304 A | 12/1997 | Telefus et al. | |
| 5,712,772 A | 1/1998 | Telefus et al. | |
| 5,777,519 A | 7/1998 | Simopoulos | |
| 5,936,446 A | 8/1999 | Lee | |
| 6,017,354 A | 1/2000 | Culp et al. | |
| 6,061,254 A | 5/2000 | Takegami | |
| 6,090,123 A | 7/2000 | Culp et al. | |
| 6,104,248 A | 8/2000 | Carver | |
| 6,329,778 B1 | 12/2001 | Culp et al. | |
| 6,440,157 B1 | 8/2002 | Shigezawa et al. | |
| 6,620,189 B1 | 9/2003 | Machold et al. | |
| 6,684,873 B1 * | 2/2004 | Anderson | F41B 11/57 |
| | | | 124/82 |
| 6,723,091 B2 | 4/2004 | Goble et al. | |
| 6,740,079 B1 | 5/2004 | Eggers et al. | |
| 6,923,804 B2 | 8/2005 | Eggers et al. | |
| 6,939,347 B2 | 9/2005 | Thompson | |
| 7,041,096 B2 | 5/2006 | Malis et al. | |
| 7,062,331 B2 | 6/2006 | Zarinetchi et al. | |
| 7,324,357 B2 | 1/2008 | Miura et al. | |
| D574,323 S | 8/2008 | Waaler | |
| 7,422,582 B2 | 9/2008 | Malackowski et al. | |
| 7,517,351 B2 | 4/2009 | Culp et al. | |
| 7,863,841 B2 | 1/2011 | Menegoli et al. | |
| 8,349,174 B2 * | 1/2013 | Bedingfield | A61M 1/16 |
| | | | 210/134 |
| 2002/0022836 A1* | 2/2002 | Goble | A61B 18/042 |
| | | | 606/34 |
| 2002/0052599 A1* | 5/2002 | Goble | A61B 18/1445 |
| | | | 606/40 |
| 2003/0181898 A1* | 9/2003 | Bowers | A61B 18/1206 |
| | | | 606/34 |
| 2004/0179829 A1* | 9/2004 | Phillips | H02P 29/02 |
| | | | 388/804 |
| 2005/0004564 A1* | 1/2005 | Wham | A61B 18/1206 |
| | | | 606/34 |
| 2005/0109111 A1 | 5/2005 | Manlove et al. | |
| 2005/0109935 A1 | 5/2005 | Manlove et al. | |
| 2006/0161148 A1* | 7/2006 | Behnke | A61B 18/1206 |
| | | | 606/34 |
| 2007/0173805 A1* | 7/2007 | Weinberg | A61B 18/1206 |
| | | | 606/34 |
| 2007/0270924 A1* | 11/2007 | McCann | A61B 18/14 |
| | | | 607/99 |
| 2008/0082095 A1* | 4/2008 | Shores | A61B 18/1206 |
| | | | 606/34 |
| 2008/0219032 A1 | 9/2008 | Stancu et al. | |
| 2009/0146635 A1 | 6/2009 | Qiu et al. | |
| 2009/0244943 A1 | 10/2009 | Yamada et al. | |
| 2009/0257254 A1 | 10/2009 | Leu | |
| 2010/0207543 A1* | 8/2010 | Crawford | H05B 33/0815 |
| | | | 315/294 |
| 2011/0071518 A1 | 3/2011 | Gilbert | |
| 2012/0095461 A1 | 4/2012 | Herscher et al. | |
| 2012/0119697 A1 | 5/2012 | Boys et al. | |
| 2012/0215216 A1* | 8/2012 | Friedrichs | A61B 18/1206 |
| | | | 606/38 |
| 2013/0066311 A1* | 3/2013 | Smith | H02H 3/08 |
| | | | 606/33 |
| 2013/0193952 A1 | 8/2013 | Krapohl | |
| 2015/0088118 A1* | 3/2015 | Gilbert | A61B 18/1206 |
| | | | 606/34 |

FOREIGN PATENT DOCUMENTS

| | | |
|---|---|---|
| CN | 204158485 U | 2/2015 |
| DE | 179607 C | 3/1905 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1519472 A1 | 3/2005 |
| EP | 1776929 A1 | 4/2007 |
| EP | 2469699 A2 | 6/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 11299237 | 10/1999 |
| JP | 2002-065690 A | 3/2002 |
| JP | 2002075750 A | 3/2002 |
| JP | 2002373812 A | 12/2002 |
| JP | 2004514398 A | 5/2004 |
| JP | 2005102750 A | 4/2005 |
| JP | 2005-185657 A | 7/2005 |
| JP | 2009261210 A | 11/2009 |
| JP | 2011223667 A | 11/2011 |
| SU | 166452 | 11/1964 |
| SU | 727201 A2 | 4/1980 |

(56) References Cited

FOREIGN PATENT DOCUMENTS

| WO | 96/39086 A1 | 12/1996 |
| WO | 02/11634 A1 | 2/2002 |
| WO | 0241482 A2 | 5/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |

OTHER PUBLICATIONS

Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Wald et al., "Accidental Burns", JAMA, Aug. 16, 1971, vol. 217, No. 7, pp. 916-921.
U.S. Appl. No. 10/406,690, filed Apr. 3, 2003, Michael S. Klicek.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/943,518, filed Jul. 16, 2013, Orszulak et al.
U.S. Appl. No. 14/069,534, filed Nov. 1, 2013, Digmann.
U.S. Appl. No. 14/096,341, filed Dec. 4, 2013, Johnson.
U.S. Appl. No. 14/098,859, filed Dec. 6, 2013, Johnson.
U.S. Appl. No. 14/100,113, filed Dec. 9, 2013, Gilbert.
U.S. Appl. No. 14/147,294, filed Jan. 3, 2014, Gilbert.
U.S. Appl. No. 14/147,312, filed Jan. 3, 2014, Gilbert.
U.S. Appl. No. 14/168,296, filed Jan. 30, 2014, Mattmiller.
U.S. Appl. No. 14/174,551, filed Feb. 6, 2014, Johnson.
U.S. Appl. No. 14/174,607, filed Feb. 6, 2014, Friedrichs.
U.S. Appl. No. 14/179,724, filed Feb. 13, 2014, Johnson.
U.S. Appl. No. 14/180,965, filed Feb. 14, 2014, Larson.
U.S. Appl. No. 14/181,114, filed Feb. 14, 2014, Larson.
U.S. Appl. No. 14/182,797, filed Feb. 18, 2014, Wham.
U.S. Appl. No. 14/183,196, filed Feb. 18, 2014, Krapohl.
U.S. Appl. No. 14/190,830, filed Feb. 26, 2014, Johnson.
U.S. Appl. No. 14/190,895, filed Feb. 26, 2014, Gilbert.
U.S. Appl. No. 14/192,112, filed Feb. 27, 2014, Weinberg.
U.S. Appl. No. 14/255,051, filed Apr. 17, 2014, Coulson.
Extended European Search Report from Appl. No. EP 14159839.1 dated Jul. 8, 2014.
Chinese Office Action and English language translation issued in Appl. No. CN 201410095399.6 dated Mar. 28, 2017.
Chinese Office Action dated Nov. 28, 2017 issued in corresponding Chinese Appln. No. 201410095399.6.
European Examination Report dated Nov. 29, 2017 issued in corresponding European Appln. No. 14159839.1.
Australian Examination Report dated Mar. 28, 2018 issued in corresponding AU Appln. No. 2014201216.
Japanese Office Action dated Jan. 31, 2018 issued in corresponding Japanese Application No. 2014-052137.
Japanese Office Action dated Dec. 7, 2018 in corresponding Japanese Patent Application No. 2014-051501, with English translation.
Rejection Decision dated Nov. 1, 2018 issued in corresponding CN Appln. No. 201410093850.
Japanese Office Action dated Nov. 1, 2018 issued in corresponding JP Appln. No. 2014-052137.
Japanese Notice of Allowance issued in corresponding JP Appln. No. 2014-052137. (Summary only).
Canadian Office Action dated Apr. 24, 2020 issued in corresponding CA Appln. No. 2,846,490.

* cited by examiner

SYSTEM AND METHOD FOR POWER CONTROL OF ELECTROSURGICAL RESONANT INVERTERS

CROSS REFERENCE TO RELATED APPLICATION

The present application claims the benefit of and priority to U.S. Provisional Application Ser. No. 61/789,005 filed on Mar. 15, 2013, the entire contents of which are incorporated herein by reference.

BACKGROUND

Technical Field

The present disclosure relates to an electrosurgical system and method for operating an electrosurgical generator. More particularly, the present disclosure relates to a system, method and apparatus for controlling electrosurgical waveforms generated by a radiofrequency resonant inverter that are suitable for arc cutting and coagulation.

Background of Related Art

Electrosurgery involves application of high radio frequency electrical current to a surgical site to cut, ablate, or coagulate tissue. In monopolar electrosurgery, a source or active electrode delivers radio frequency alternating current from the electrosurgical generator to the targeted tissue and a return electrode conducts the current back to the generator. A patient return electrode is placed remotely from the active electrode to conduct the current back to the generator.

In bipolar electrosurgery return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like. A forceps is a pliers-like instrument which relies on mechanical action between its jaws to grasp, clamp and constrict vessels or tissue. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue. However, the above example is for illustrative purposes only and there are many other known bipolar electrosurgical instruments which are within the scope of the present disclosure.

Electrosurgical procedures outlined above may utilize various tissue and energy parameters in a feedback-based control system. There is continual need to improve delivery of energy to the tissue.

SUMMARY

The present disclosure provides a method for controlling an electrosurgical generator. The method including: generating the at least one electrosurgical waveform through an RF output stage including a pulse-width-modulator coupled to an RF inverter, which is coupled to a power source configured to output DC current; applying at least one electrosurgical waveform to tissue through at least one electrode, the at least one electrosurgical waveform including a plurality of cycles; measuring a voltage and a current of the at least one electrosurgical waveform; calculating at least one of a voltage limit or a current limit; and supplying a control signal to the pulse-width modulator based on at least one of the voltage limit or the current limit to saturate the RF output stage based on the voltage-current characteristics of the RF output stage.

According to additional aspects of the above embodiment, the RF output stage includes at least one switching element coupled to a controller.

According to additional aspects of the above embodiment, the controller includes a proportional-integral-derivative controller and a pulse-width-modulator, wherein the pulse-width-modulator is configured to output the control signal to the at least one switching element and adjust a duty cycle of the control signal based on an output of proportional-integral-derivative controller.

According to additional aspects of the above embodiment, the controller is configured to determine impedance based on the measured voltage and current.

According to additional aspects of the above embodiment, the proportional-integral-derivative controller is configured to provide the output based on the impedance.

According to additional aspects of the above embodiment, the proportional-integral-derivative controller includes a voltage limiter function.

According to additional aspects of the above embodiment, the proportional-integral-derivative controller includes a current limiter function.

According to additional aspects of the above embodiment, the method further includes generating DC current at power supply coupled to the RF output stage; and supplying the control signal to the power supply based on at least one of the voltage limit or the current limit to saturate the RF output stage based on the voltage-current characteristics of the RF output stage.

The present disclosure also provides an electrosurgical generator, including: an RF output stage configured to generate at least one electrosurgical waveform including a plurality of cycles; at least one sensor coupled to the RF output stage, the at least one sensor configured to measure a voltage and a current of the at least one electrosurgical waveform; and a controller coupled to the at least one sensor and the RF output stage, the controller including a proportional-integral-derivative controller having at least one of voltage limiter or a current limiter, the proportional-integral-derivative controller configured saturate the RF output stage based on the voltage-current characteristics of the RF output stage.

According to additional aspects of the above embodiment, the RF output stage includes an RF inverter coupled to a power source configured to output DC current.

According to additional aspects of the above embodiment, the RF inverter includes at least one switching element coupled to the controller.

According to additional aspects of the above embodiment, the controller includes a pulse-width-modulator configured to output a control signal to the at least one switching element and adjust a duty cycle of the control signal based on an output of proportional-integral-derivative controller.

According to additional aspects of the above embodiment, the controller is configured to determine impedance based on the measured voltage and current.

According to additional aspects of the above embodiment, the proportional-integral-derivative controller is configured to provide the output based on the impedance.

According to additional aspects of the above embodiment, the controller is further configured to increase the current of the at least one electrosurgical waveform to increase the generation of the electrical discharges.

According to additional aspects of the above embodiment, the generator further including a power supply having an AC-DC converter coupled to the RF output stage, wherein the RF output stage includes an DC-AC inverter.

According to additional aspects of the above embodiment, the controller is coupled to the DC-AC inverter.

According to additional aspects of the above embodiment, the power supply further includes a DC-DC converter coupled to the AC-DC converter and the RF output stage, the DC-DC converter being coupled to and controllable by the controller.

The present disclosure also provides an electrosurgical system, including: an electrosurgical generator having: a power supply configured to output DC current; an RF output stage coupled to the power supply, the power supply including at least one switching element configured to generate at least one electrosurgical waveform including a plurality of cycles from the DC current; at least one sensor coupled to the RF output stage, the at least one sensor configured to measure a voltage and a current of the at least one electrosurgical waveform; and a controller coupled to the at least one sensor and at least one of the RF output stage or the power supply, the controller including a proportional-integral-derivative controller having at least one of voltage limiter or a current limiter, the proportional-integral-derivative controller configured to saturate at least one of the RF output stage or the power supply based on the voltage-current characteristics of the RF output stage.

The system also includes at least one electrosurgical instrument configured to couple to the electrosurgical generator and to supply the at least one electrosurgical waveform to a tissue.

According to additional aspects of the above embodiment, wherein the controller is configured to determine impedance based on the measured voltage and current and the proportional-integral-derivative controller is configured to provide the output based on the impedance.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure can perform monopolar and/or bipolar electrosurgical procedures, including, for example, cutting, coagulation, ablation, and vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
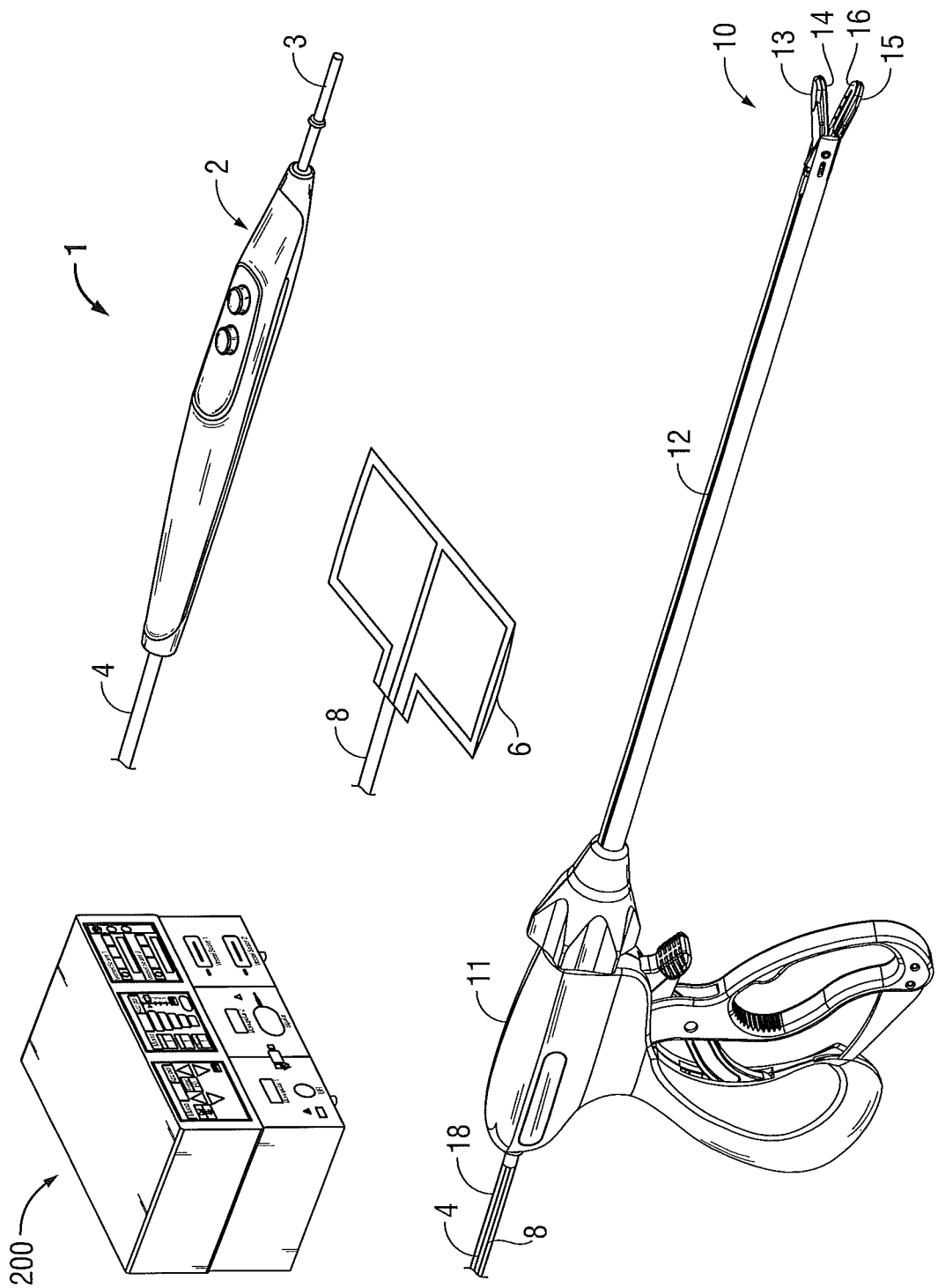
FIG. 1 is a perspective view of the components of one illustrative embodiment of an electrosurgical system according to the present disclosure.

FIG. 1 is a schematic illustration of a bipolar and monopolar electrosurgical system 1 according to the present disclosure. The system 1 may include one or more monopolar electrosurgical instruments 2 having one or more active electrodes 3 (e.g., electrosurgical cutting probe, ablation electrode(s), etc.) for treating tissue of a patient. Electrosurgical alternating current is supplied to the instrument 2 by a generator 200 via a supply line 4 that is connected to an active terminal 230 (FIG. 3) of the generator 200, allowing the instrument 2 to cut, coagulate, ablate and/or otherwise treat tissue. The alternating current is returned to the generator 200 through a return electrode 6 via a return line 8 at a return terminal 232 (FIG. 3) of the generator 200. For monopolar operation, the system 1 may include a plurality of return electrode pads 6 that, in use, are disposed on a patient to minimize the chances of tissue damage by maximizing the overall contact area with the patient. In addition, the generator 200 and the return electrode pads 6 may be configured for monitoring so-called "tissue-to-patient" contact to insure that sufficient contact exists therebetween to further minimize chances of tissue damage.

Figure 3:
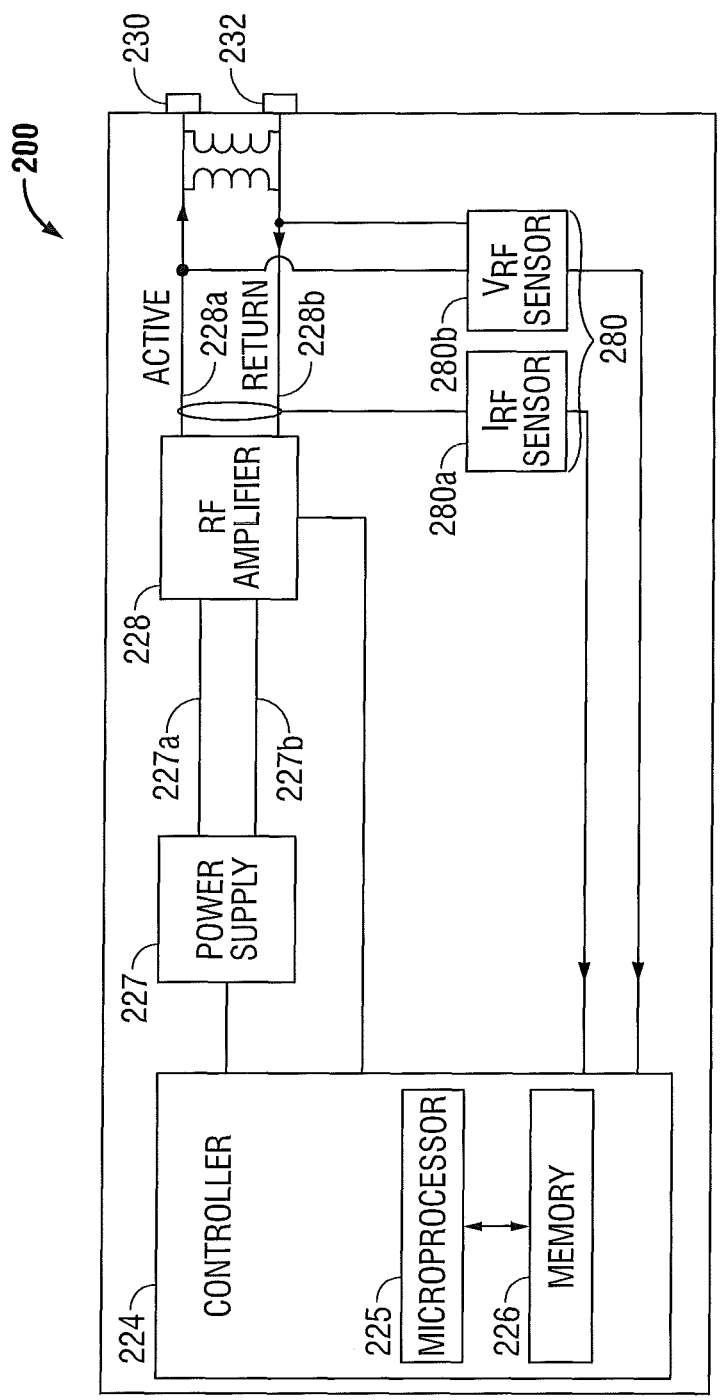
FIG. 3 is a schematic, block diagram of the embodiment of an electrosurgical generator of FIG. 2 according to the present disclosure.

The system 1 may also include one or more bipolar electrosurgical instruments, for example, a bipolar electrosurgical forceps 10 having one or more electrodes for treating tissue of a patient. The electrosurgical forceps 10 includes a housing 11 and opposing jaw members 13 and 15 disposed at a distal end of a shaft 12. The jaw members 13 and 15 have one or more active electrodes 14 and a return electrode 16 disposed therein, respectively. The active electrode 14 and the return electrode 16 are connected to the generator 200 through cable 18 that includes the supply and return lines 4, 8 coupled to the active and return terminals 230, 232, respectively (FIG. 3). The electrosurgical forceps 10 is coupled to the generator 200 at a connector having connections to the active and return terminals 230 and 232 (e.g., pins) via a plug disposed at the end of the cable 18, wherein the plug includes contacts from the supply and return lines 4, 8 as described in more detail below.

Figure 2:
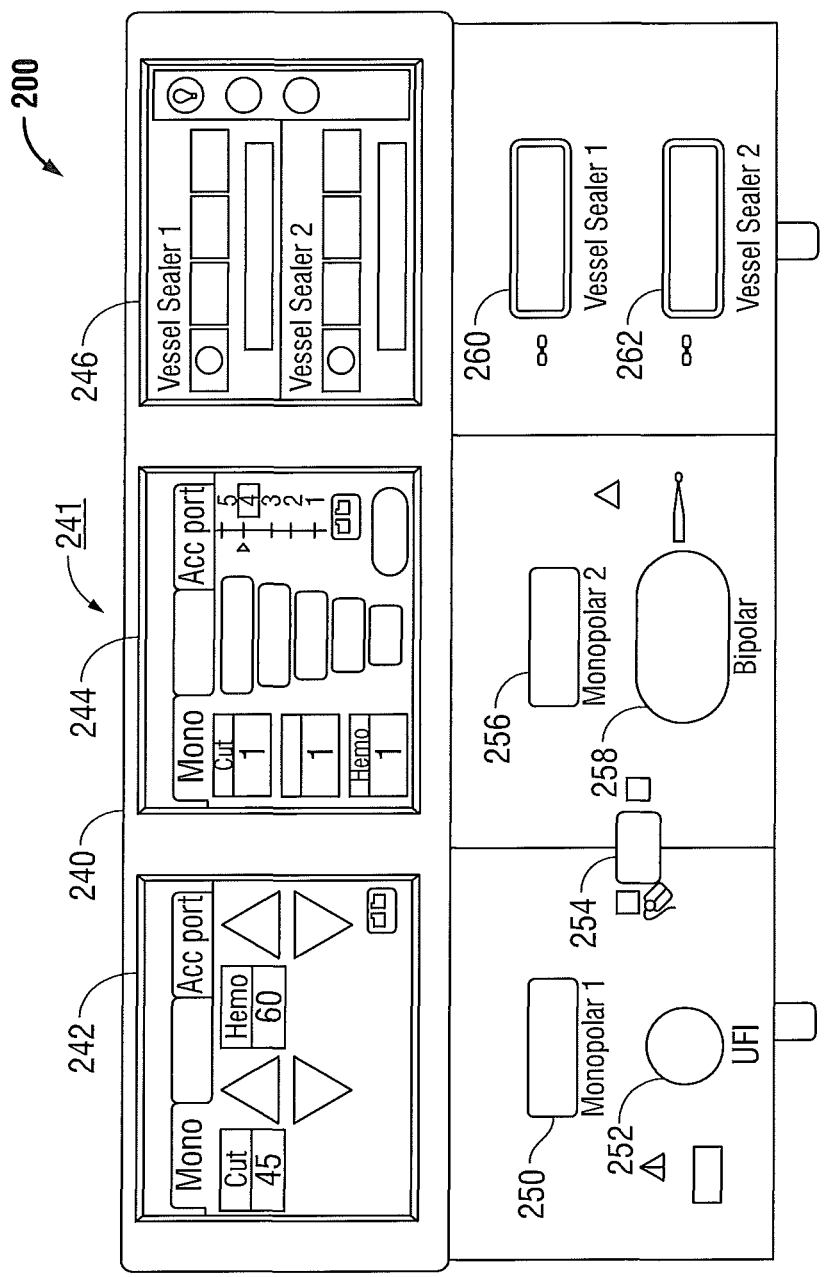
FIG. 2 is a front view of one embodiment of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250, 252, 254, 256, 258, 260, 262 to accommodate various types of electrosurgical instruments (e.g., electrosurgical forceps 10, etc.).

The generator 200 includes a user interface 241 having one or more display screens or information panels 242, 244, 246 for providing the user with variety of output information (e.g., intensity settings, treatment complete indicators, etc.). Each of the screens 242, 244, 246 is associated with corresponding connector 250, 252, 254, 256, 258, 260, 262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then adjusts inputs by simply touching corresponding menu options.

Screen 242 controls monopolar output and the devices connected to the connectors 250 and 252. Connector 250 is configured to couple to a monopolar electrosurgical instrument (e.g., electrosurgical instrument 2) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to the controller 224 where the setting may be saved in memory 226. In embodiments, the intensity setting may be a number scale, such as for example, from one to ten or one to five. In embodiments, the intensity setting may be associated with an output curve of the generator 200. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. The generator 200 includes a controller 224, a power supply 227, and a radio-frequency (RF) amplifier 228. The power supply 227 may be a high voltage, DC power supply that connects to an AC source (e.g., line voltage) and provides high voltage, DC power to the RF amplifier 228 via leads 227a and 227b, which then converts high voltage, DC power into treatment energy (e.g., ultrasonic, electrosurgical or microwave) and delivers the energy to the active terminal 230. The energy is returned thereto via the return terminal 232. The active and return terminals 230 and 232 and coupled to the RF amplifier 228 through an isolation transformer 229. The RF amplifier 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or RF amplifier 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or RF amplifier 228, which adjusts the DC and/or power supply, respectively. Those skilled in the art will appreciate that the processor 225 may be substituted by using any logic processor (e.g., control circuit) adapted to perform the calculations and/or set of instructions described herein including, but not limited to, field programmable gate array, digital signal processor, and combinations thereof.

The generator 200 according to the present disclosure includes a plurality of sensors 280, e.g., an RF current sensor 280a, and an RF voltage sensor 280b. Various components of the generator 200, namely, the RF amplifier 228, the RF current and voltage sensors 280a and 280b, may be disposed on a printed circuit board (PCB). The RF current sensor 280a is coupled to the active terminal 230 and provides measurements of the RF current supplied by the RF amplifier 228. The RF voltage sensor 280b is coupled to the active and return terminals 230 and 232 provides measurements of the RF voltage supplied by the RF amplifier 228. In embodiments, the RF current and voltage sensors 280a and 280b may be coupled to active and return leads 228a and 228b, which interconnect the active and return terminals 230 and 232 to the RF amplifier 228, respectively.

The RF current and voltage sensors 280a and 280b provide the sensed RF voltage and current signals, respectively, to the controller 224, which then may adjust output of the power supply 227 and/or the RF amplifier 228 in response to the sensed RF voltage and current signals. The controller 224 also receives input signals from the input controls of the generator 200, the instrument 2 and/or forceps 10. The controller 224 utilizes the input signals to adjust power outputted by the generator 200 and/or performs other control functions thereon.

Figure 4A:
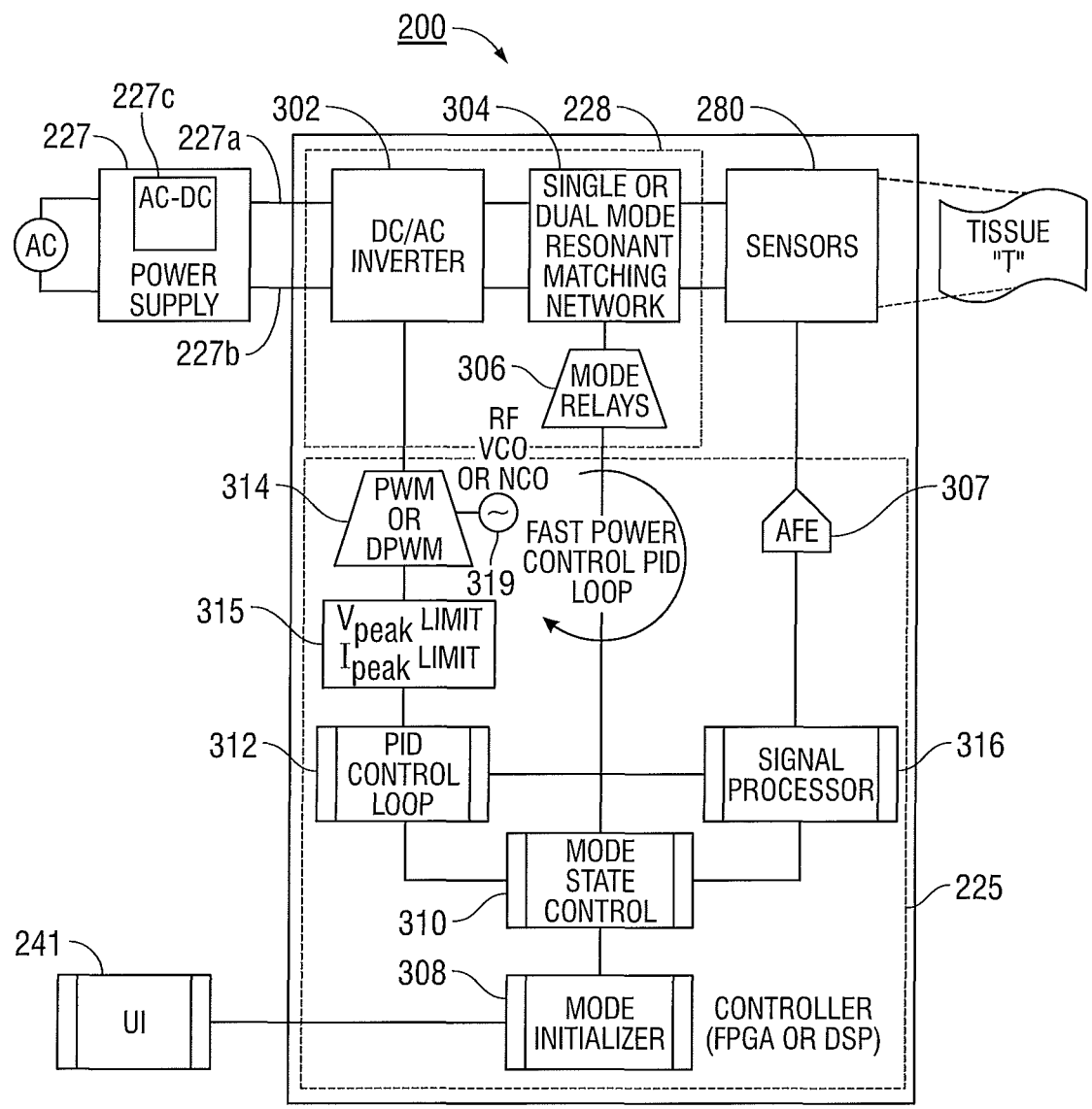
FIGS. 4A and 4B are schematic, block diagrams of other illustrative embodiments of the electrosurgical generator of FIG. 2 according to the present disclosure.

FIG. 4A shows another embodiment of the generator 200 based on a Class S, high-efficiency, pulse width modulation inverter. An example embodiment based on an analog pulse width modulator that utilized this configuration is disclosed in a commonly-owned U.S. Patent Publication No. 2006/0161148, the entire contents of which are incorporated by reference herein. In this illustrative embodiment, the power supply 227 is a fixed output AC-DC converter 227c coupled to a source of AC energy as described above, which is in turn, coupled to the RF amplifier 228.

Figure 4B:
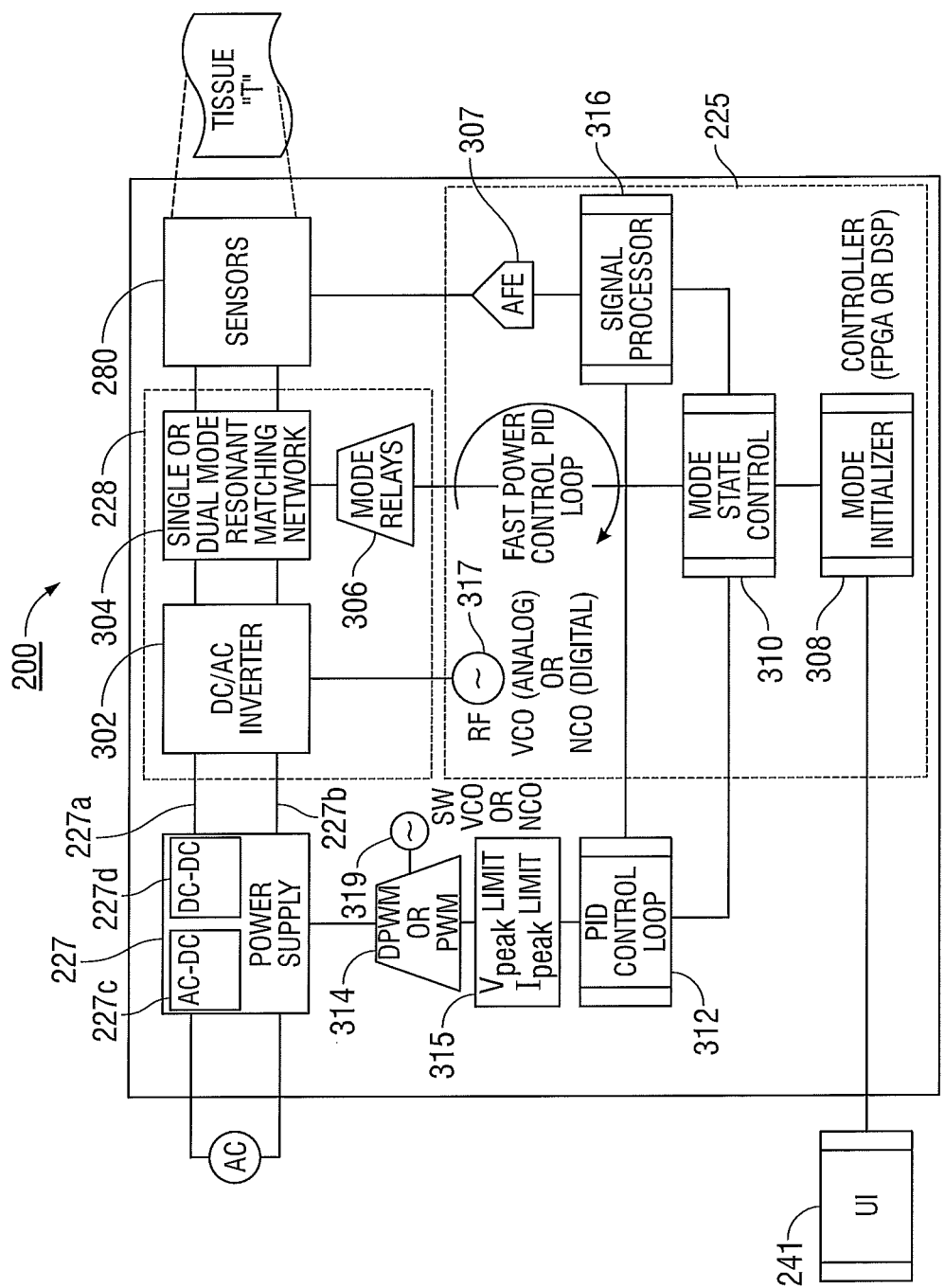

FIG. 4B shows yet another embodiment of the generator 200 based on a modified Kahn technique of amplitude modulation. In this illustrative embodiment, the power supply 227 is a fixed output AC-DC converter 227c that is further enhanced by a variable DC-DC converter 227d. The variable DC-DC converter 227d of power supply 227 may be configured to any suitable topology including, but not limited to, resonant, non-resonant, synchronous, non-synchronous, buck, boost, buck-boost, and the like.

With continued reference to FIGS. 4A-4B, the RF amplifier 228 may include a DC-AC inverter 302 coupled to a resonant matching network 304. As shown in FIG. 4A, the control input for the RF amplifier 228 may be an analog-based PWM or a digitally-based DPWM 314. In the Class S, high efficiency, pulse width modulation technique the generator output amplitude is varied by varying the pulse widths at the inverter operating frequency (e.g. 472 kHz) and relying upon the resonant matching network 304 to smooth the output to about a sinusoidal shape. The DPWM 314 is coupled to an oscillator 319, which may be an analog voltage-controlled oscillator (VCO) or a numerically-controlled oscillator (NCO). In this embodiment, the oscillator 319 operates at a radio frequency ("RF") (e.g., therapeutic frequency) suitable for controlling the DC-AC inverter 302. The DPWM 314 is coupled to the inverter 302 of the RF amplifier 304. The DPWM 314 is configured to control one or more switching components of the RF amplifier 304 to invert DC current into RF current as described in further detail.

As shown in FIG. 4B, the control input from the PWM or the digitally-based DPWM 314 is supplied to the power supply 227. In the modified Kahn technique the input to the RF amplifier 228 at the DC-AC inverter 302 is a fixed-pulse width (e.g. for optimized efficiency at 472 kHz) resulting in about a sinusoidal output after passing through the resonant matching network 304 and the generator output amplitude is varied by varying the power supply 227 output. In this embodiment, the power supply 227 is controlled by the DPWM 314. The DPWM 314 is coupled to the oscillator 319, which may be an analog voltage-controlled oscillator (VCO) or a numerically-controlled oscillator (NCO). The input at the DC-AC inverter 302 may be provided by an oscillator 317, which may be an analog voltage-controlled oscillator (VCO) or a numerically-controlled oscillator (NCO). The oscillator 317 operates at a radio frequency ("RF") (e.g., therapeutic frequency) suitable for controlling the DC-AC inverter 302 and the oscillator 319 operates at a switching ("SW") frequency suitable for controlling the power supply 227.

With continued reference to FIGS. 4A-4B, which with the exception for the differences described above otherwise share the same components and design, the inverter 302 may be configured according to any suitable topology including, but not limited to, half-bridge, full-bridge, push-pull, and the like. The resonant matching network 304 may be a single or dual mode resonant network having any suitable combination of LC (inductor-capacitor) filters/resonators and other passive electrical components for matching the output of the RF amplifier 228. The RF amplifier 228 also includes a plurality of mode relays 306. Mode relays 306 are coupled to the plurality of connectors 250, 252, 254, 256, 258, 260, 262 for controlling the supply of electrosurgical energy to desired connectors such that only the desired connectors 250, 252, 254, 256, 258, 260, 262 are energized at any specific time.

The processor 225 is coupled to the user interface 241 and is configured to modify modes, energy settings, and other parameters of the generator 200 in response to user input. The processor 225 includes a mode initializer 308 which is configured to initialize a selected operating mode. The generator 200 is configured to operate in a variety of modes. In one embodiment, the generator 200 may output the following modes: cut, blend, coagulate, division with hemostasis, fulgurate, spray, combinations thereof, and the like. Each mode operates based on a pre-programmed power curve that controls the amount of power that is output by the generator 200 at varying impedances of the load (e.g., tissue). Each power curve includes power, voltage and current control ranges that are defined by the user-selected power setting and the measured impedance of the load.

In the cut mode, the generator 200 may supply a continuous sine wave output having a plurality of RF cycles at a predetermined frequency (e.g., 472 kHz) with a crest factor of about 1.414 over an impedance range of from about 100Ω to about 2,000Ω. The cut mode power curve may include three regions: constant current into low impedance, constant power into medium impedance and constant voltage into high impedance. In the blend mode, the generator may supply alternating bursts of a sine wave output at a predetermined periodic rate, with the burst cycles reoccurring at a first predetermined rate (e.g., about 26.21 kHz), each burst cycle includes a plurality of sine wave RF cycles at the predetermined frequency (e.g., 472 kHz). In one embodiment, the duty cycle of the bursts may be about 50%. In other words, for each burst cycle the power is on for 50% of the time and it is off for 50% of the time. The crest factor of one period of the sine wave output may be about 1.414. The crest factor of one burst cycle may be about 2.7.

The division with hemostasis mode may include bursts of sine wave outputs at a predetermined frequency (e.g., 472 kHz) reoccurring at a second predetermined rate (e.g., about 28.3 kHz). The duty cycle of the bursts may be about 25%, i.e. the power is on for 25% of each cycle and off for the remaining 75% of the cycle. The crest factor of one burst cycle may be about 4.3 across an impedance of from about 100Ω to about 2,000Ω. The fulgurate mode may include bursts of sine wave outputs at a predetermined frequency (e.g., 472 kHz) reoccurring at a third predetermined rate (e.g., about 30.66 kHz). The duty cycle of the bursts may be about 6.5% and the crest factor of one burst cycle may be about 5.55 across an impedance range of from about 100Ω to about 2,000Ω. The spray mode may include bursts of a sine wave output at a predetermined frequency (e.g., 472 kHz) reoccurring at a fourth predetermined rate (e.g., about 21.7 kHz). The duty cycle of the bursts may be about 4.6% and the crest factor of one burst cycle may be about 6.6 across the impedance range of from about 100Ω to about 2,000Ω.

The processor 225 further includes a mode state control 310 which is configured to maintain energy output of the generator 200 according to the parameters set by the mode initializer 308. The mode state control 310 controls the RF amplifier 228 based on the sensor signals from the sensors 280 using a proportional-integral-derivative (PID) control loop 312 with a control output limited by a voltage and/or current output amplitude limiter function 315 that includes saturation and integral anti-windup capabilities for the PID implemented in the processor 225.

The processor 225 includes an analog front-end (AFE) 307 for interfacing between the sensors 280 and the signal processor 316. The AFE 307 may include a plurality of analog-to-digital converters and other circuit components for receiving and converting analog signals from the sensors into digital counterparts thereof. The AFE 307 provides the digitized sensor signals to a signal processor 316. The signal processor 316 may also calculate various energy and/or tissue properties based on sensor signals including, but not limited to, impedance, voltage, current, power, time duration, as well as instantaneous, average, root-mean-square values, and combinations thereof.

The generator 200 provides closed-loop control of various electrosurgical modes, e.g., arc cutting and coagulation, based on current, power and voltage bounds inherent to voltage-current characteristics of a resonant inverter of the RF amplifier 228. The voltage-current characteristic of any resonant inverter, when plotted, forms an ellipse bounded by voltage and current limited regions due to the output impedance of the resonant network. This output impedance of the inverter may be designed to be centered upon the geometric mean of the expected minimum to maximum terminating resistances observed during operation in the electrosurgical mode (e.g. the resistance of the tissue). The operating characteristics of the RF amplifier 228 may then be aligned to coincide with the maximum voltage and current of the particular power setting requested by the user.

Conventional generators supply electrosurgical energy to tissue at constant power over some specified range of load resistance. Closed-loop control algorithms have been introduced since open-loop control algorithms were insufficient for covering a wide range of tissue impedance loads encountered during various surgical procedures. In certain embodiments, a combination of open and closed loop controls were utilized as disclosed in a commonly-owned U.S. Patent Publication No. 2006/0161148, the entire contents of which are incorporated by reference herein.

Certain modes, such as arc cut and coagulation modes, present a unique problem for closed-loop control using a voltage-source-based inverter. During operation, arcing is generated to achieve desired surgical effects. High arc currents are well-suited for their hemostasis effects; however, to limit thermal transfer, it is also desirable to also limit arcing. In particular, arcing in the coagulation modes is interrupted to provide for high enough instantaneous power to create hemostasis, while keeping average power low enough to minimize thermal spread. The present disclosure provides for inverters that are configured to control arcing to achieve these goals with a minimal amount of required heuristics or state changes performed by the mode state control 310 and/or the PID 312. In particular, the present disclosure provides for inverters that accomplish this by maintaining zero-voltage switching for all loads at all amplitudes, maintaining constant power over a desired range of tissue impedances, and limiting the current and voltage using the saturation and integral anti-windup capabilities of the PID controller by taking advantage of the voltage-current lossless output characteristic of the RF amplifier 228 at a predetermined maximum control output amplitude.

Figure 5:
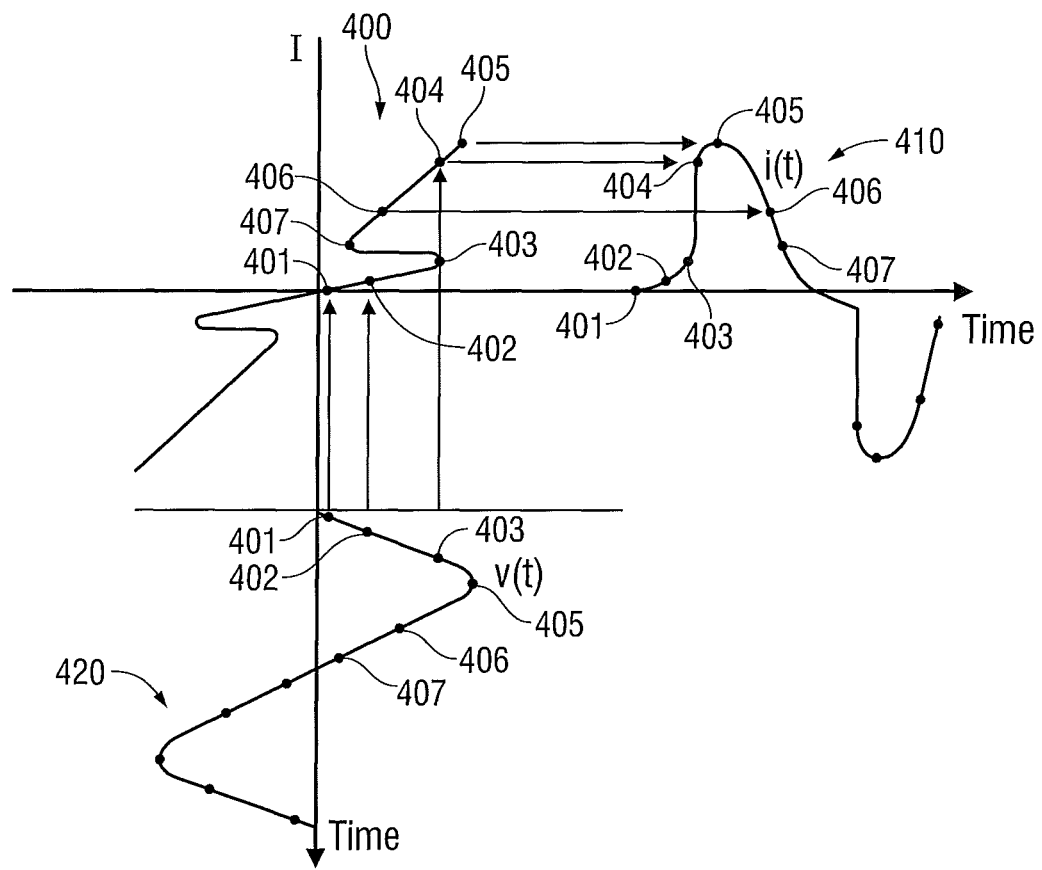
FIG. 5 is a plot of a voltage and current illustrating electrical discharges according to an embodiment of a voltage source of the present disclosure.

The RF amplifier 228 operates within its lossless voltage-current output characteristic ellipse substantially as a voltage, power or current source depending on the terminating load resistance. With respect to FIG. 5, an arc discharge from a voltage source, e.g., RF amplifier 228, is shown as a current plot 400 as a function of voltage and as a current plot 410 and a voltage plot 420 as a function of time at a time scale of the predetermined frequency (e.g., 472 kHz). For simplicity, only the positive half-cycle is going to be described. At point 401 the voltage supplied to tissue is insufficient to provide for current flow and is in a sub-saturation current region. As the plots 400, 410, 420 progress to point 402 and toward point 403 the discharge transitions from a Townsend effect to corona discharge to the glow discharge. In this region the current is still relatively low with respect to other points and no power is dissipated by the arc. However, once the arc jumps the gap between the electrode (e.g., electrode 3) and the tissue, current immediately flows at point 404 along a new load line, which overlaps point 403 on the voltage plot 420. More voltage beyond point 404 provides for a linear increase in current to point 405 at the peak. As the voltage is decreased at point 406, the arcing is sustained, rather than spontaneously returning to point 403. Voltage is decreased linearly until the point 407, during which the arc is extinguished and the process for arc initiation would need to be repeated as described above. The voltage and current characteristics are similar for the negative cycle. The arc may be extinguished unless there is an excess of low frequency RF or DC charge available at the electrode thereby acting as a bias charge producing non-symmetrical negative half-cycle plots.

Figure 6:
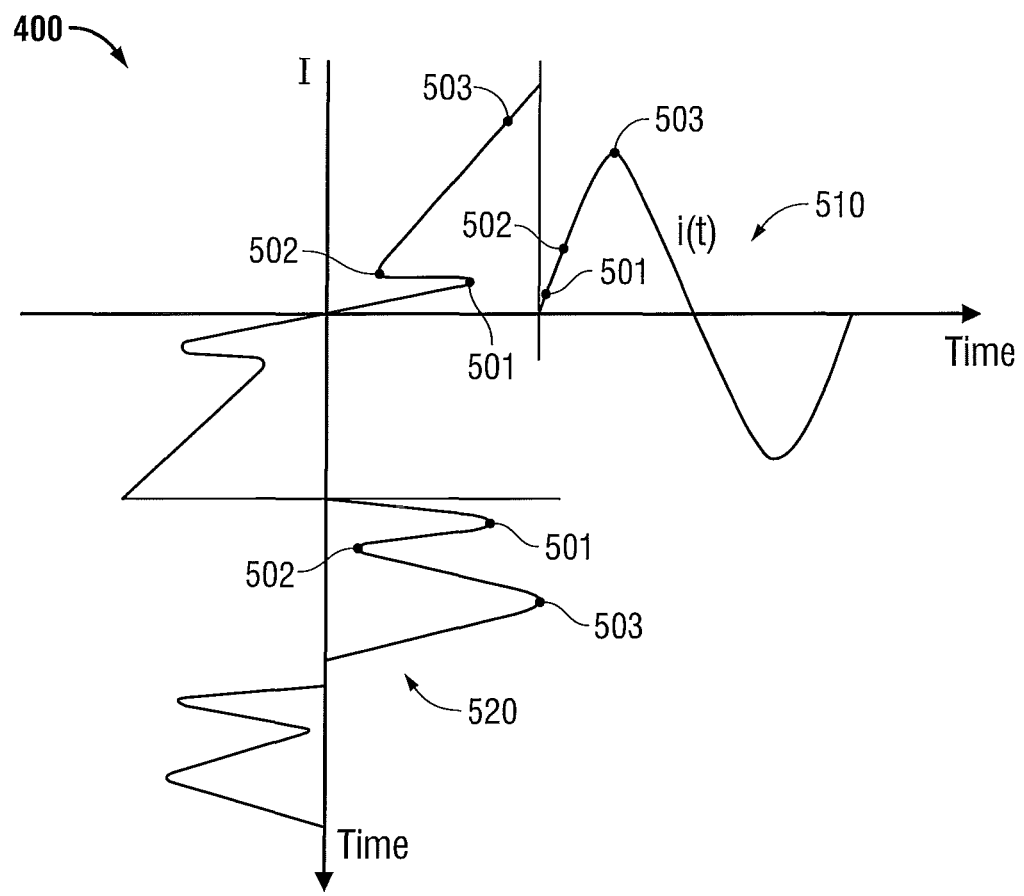
FIG. 6 is a plot of a voltage and current illustrating electrical discharges according to an embodiment of a current source inverter of the present disclosure.

With respect to FIG. 6, an arc discharge from a current source, e.g., RF amplifier 228, is shown as a current plot 500 as a function of voltage and as current and voltage plots 510, 520 as a function of time at a time scale of the predetermined frequency (e.g., 472 kHz). For simplicity, only the positive half-cycle is going to be described. The current source may provide higher output power, e.g., more power efficient, than a voltage source at the same peak current. As the current is increased, voltage is increased accordingly, until point 501, when continual increase in current results in a voltage drop at point 502. As current is decreased at point 503, the voltage increases to another peak. The voltage and current characteristics are similar for the negative cycle.

Figure 7A:
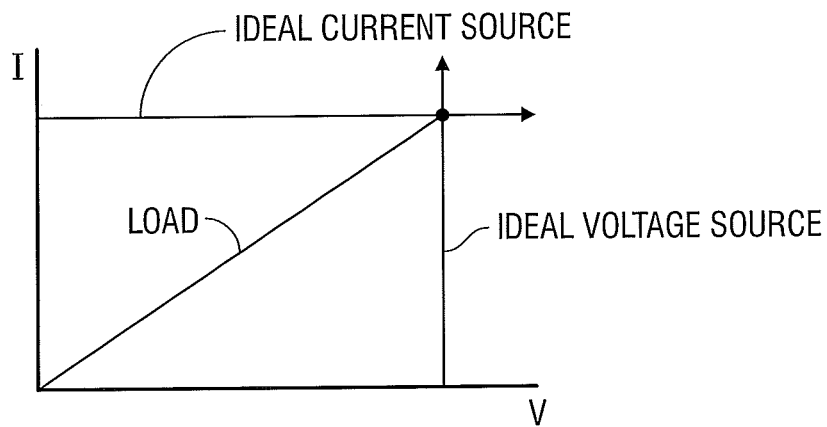
FIG. 7A is a plot of voltage and current illustrating ideal output of voltage and current sources according to an embodiment of the present disclosure.
Figure 7B:
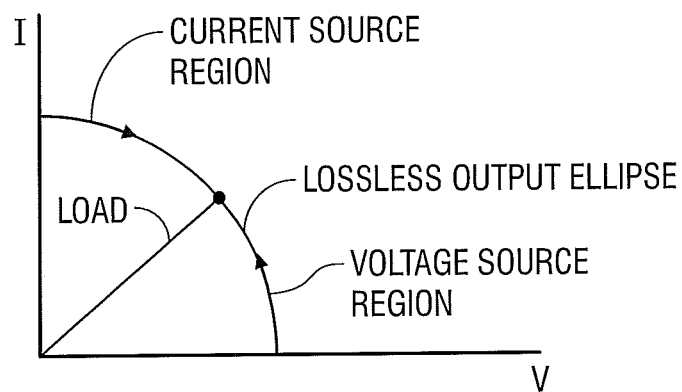
FIG. 7B is a plot of voltage and current illustrating lossless output of voltage and current sources according to an embodiment of the present disclosure.
Figure 7C:
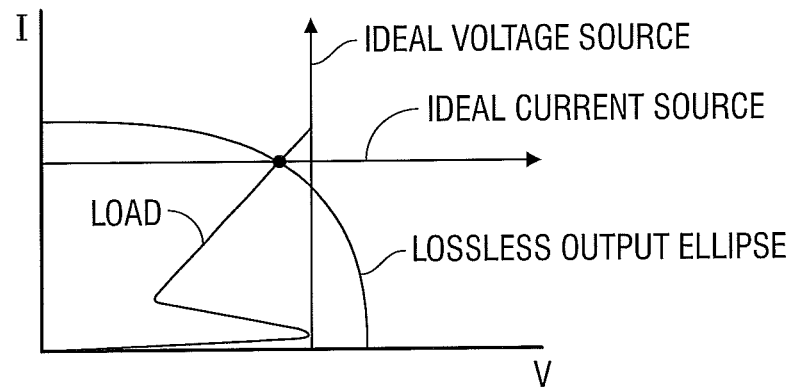
FIG. 7C is an overlapping plot of voltage and current illustrating ideal, lossless, and arcing output of voltage and current sources according to an embodiment of the present disclosure.

Maximum power transfer from a power source, e.g. RF amplifier 228, occurs at its matched impedance, when the output impedance is substantially the same as the load impedance. Ideal voltage and current sources do not have Thevenin and Norton equivalent source impedances as illustrated in FIG. 7A, which shows a current plot as a function of voltage. A lossless matching network added to an ideal Thevenin or Norton source has a substantially elliptically shaped curve as shown in FIG. 7B, which shows a current plot as a function of voltage. The present disclosure provides for an RF amplifier 228 having a continuously variable voltage-current response (e.g., characteristic) with a control loop limit for the voltage and current that simultaneously attempts to encompass the voltage-current response of an arc as shown in FIG. 7C, which shows a current plot as a function of voltage that operates within the parameters of ideal and lossless voltage/current sources of FIG. 7A and FIG. 7B, operates at the desired current, voltage, or power point determined by the load, user setting and/or mode, and limits the voltage and current with the lossless matching network characteristic rather than actively controlling the voltage or current as done in prior art. The elliptical voltage-current response may be varied by changing the equivalent amplitude of the output of the DC-AC inverter 302 either by varying the pulse widths of the DC-AC inverter 302, varying the frequency of the DC-AC inverter 302 to substantially change the output resistance and voltage transfer ratio of the resonant matching network 304, varying the pulse widths of the power supply 227 DC-DC converter, or some combination therein. The intersection of the load line with the elliptical voltage-current response ultimately determines the operating point of the generator into the load.

Figure 7D:
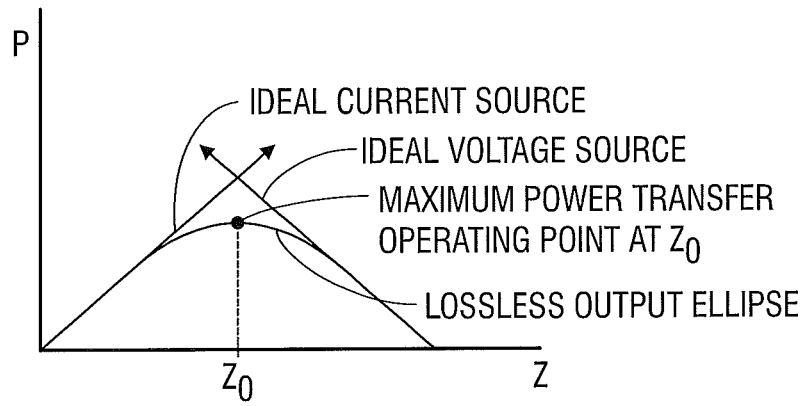
FIG. 7D is a plot of power and impedance illustrating ideal and lossless output of voltage and current sources according to an embodiment of the present disclosure.

Maximum power transfer for ideal voltage and current sources may also be represented as a power plot as a function of impedance as illustrated in FIG. 7D. For ideal current and voltage sources power increases continuously unless output device saturation is limited. Power, voltage, and current may be limited by matching impedance. However, even for well-matched voltage sources arcing may result in excessive power output due to insufficient limits.

In embodiments, arc control may be accomplished by measuring and limiting instantaneous current, voltage, and/or power using very high sample rates, e.g., digital sampling combined with correspondingly fast circuit components for limit current, e.g., current foldback circuitry as described in more detail below. In further embodiments, matched impedance may be increased and the RF amplifier 228 may be operated as a current source. In particular, output impedance may be increased to be higher than the expected impedance during arcing. Output impedance may be from about two to about six times higher than the highest expected impedance, in embodiments output impedance may be about four times higher than expected impedance. This provides a natural power limiting function once voltage is limited.

Figure 8:
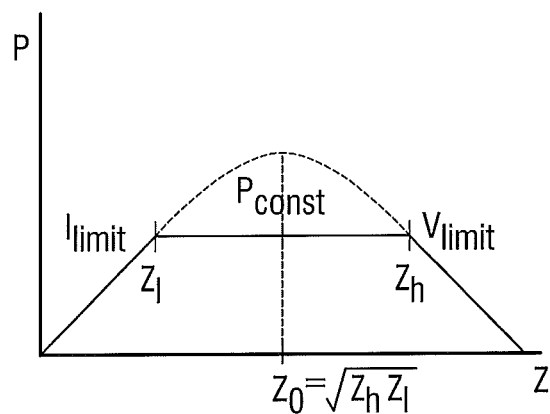
FIG. 8 is a constant power plot of a generator output according to an embodiment of the present disclosure.

In another embodiment, output impedance may include multiple output impedances that are selected by the user and/or the generator 200 depending on the tissue type. In a further embodiment, characteristic output impedance of the generator 200 may be selected to be a geometric mean of maximum and minimum impedances and limited maximum output amplitude of the DC-AC inverter 302 such that the elliptical voltage-current response occurs at the coincidence of the current and voltage limits as illustrated in FIG. 8.

Figure 9:
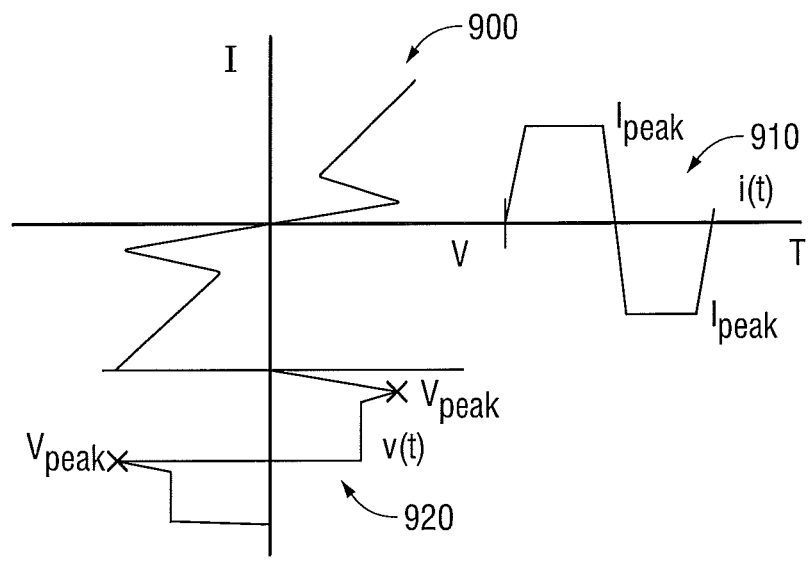
FIG. 9 is a plot of a voltage and current illustrating electrical discharges according to an embodiment of the present disclosure.

In specific embodiments, the RF amplifier 228 may be configured as a square wave current source. Waveform characteristics of a square-wave current source are shown in FIG. 9 as a current plot 900 as a function of voltage and as a current plot 910 and a voltage plot 920 as a function of time at a time scale of the predetermined frequency (e.g., 472 kHz).

Figure 10:
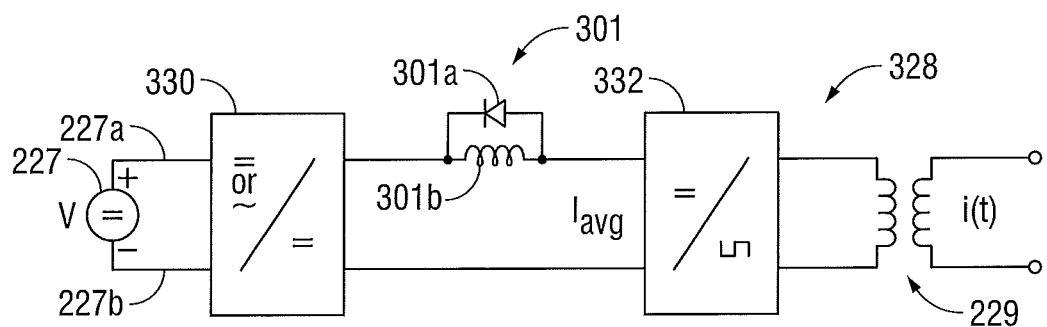
FIG. 10 is a schematic diagram of an RF amplifier of the generator of FIG. 2 according to an embodiment of the present disclosure.

FIG. 10 shows an embodiment of an RF amplifier 328 that is an amplitude-limited current-source inverter configured to variably limit peak voltage to prevent conduction of arcs at certain distances between the tissue and the active electrode 2. The RF amplifier 328 generates square-wave current as shown in FIG. 9 and includes a converter 330 that is coupled to the power supply 227, which may be a DC or AC supply, via leads 227a and 227b and is, in turn, coupled to a converter 330 and an inverter 332. The inverter 332 is, in turn, coupled to the transformer 229. The converter 330 converts the AC or DC output of the power supply 227 into a DC output. The converter 330 is configured to limit voltage peaks whereas the inverter 332 is configured to chop and steer the current from the link inductor 301b. The RF amplifier 328 also includes a voltage limiting circuit 301 having a diode 301a that is coupled in parallel with an inductor 301b. The voltage limiting circuit 301 is limited to the output of the converter 330. The converter 330 and inverters 332 may be configured as any suitable converter/inverter combinations including, but not limited to, isolated, non-isolated, full-bridge, half-bridge, synchronous, asynchronous, Buck, boost, Buck-boost, and combinations thereof.

Figure 11:
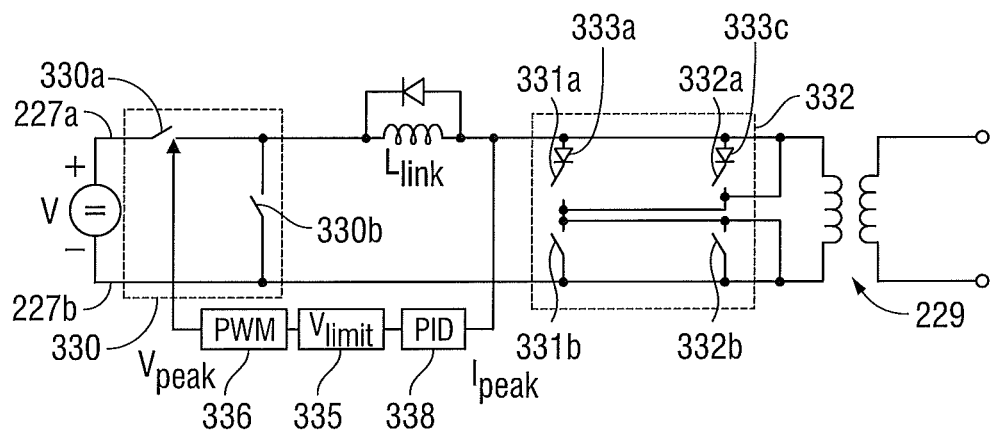
FIG. 11 is a schematic diagram of an RF amplifier of the generator of FIG. 2 according to an embodiment of the present disclosure.

FIG. 11 shows another embodiment of the RF amplifier 328. The converter 330 is shown as a half-bridge inverter and includes a first switching element 330a and a second switch 330b. The first switching element 330a is disposed on the lead 227a and the second switch 227b interconnects the leads 227a and 227b. Operation of the switching elements 330a and 330b is controlled via a pulse width modulator (PWM) 336 and a proportional-integral-derivative controller 338 whereby the output voltage of the converter 330 is limited by a voltage limiter function 335 for the PID controller 338, which includes saturation and integral anti-windup capability, based on when the limiter is actively limiting. The PWM 336 and the PID controller 338 may be configured within the controller 224. The voltage limiter 335 may be embodied as a software algorithm in the controller 224. As shown in FIG. 11, the inverter 332 is configured as a full-bridge inverter having a first pair of switching elements 331a and 331b and a second pair of switching elements 332a and 332b that are coupled to the transformer 229. Each of the switching elements 331a and 332a is coupled to the steering diodes 333a and 333c. The PID controller 338 receives a feedback signal from the voltage limiting circuit 301 allowing the PID controller 338 to control the switching elements 330a, 330b, 331a, 331b, 332a, 332b, in response thereto. In particular, the PID controller 338 controls the current and limits the voltage based on the instructions of the voltage limiter 335 and provides a control signal to the PWM 336, which in turn provides the activation signals (e.g., on/off periods) to the switching elements 330a, 330b, 331a, 331b, 332a, 332b on a per RF cycle basis.

Figure 12:
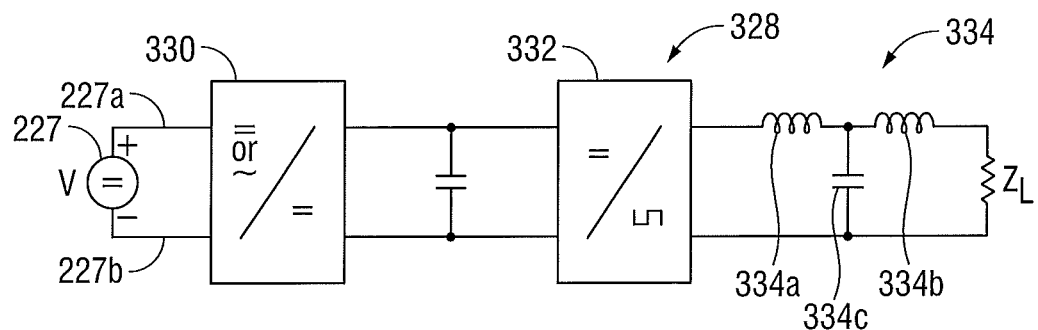
FIG. 12 is a schematic diagram of an RF amplifier of the generator of FIG. 2 according to an embodiment of the present disclosure.

FIG. 12 illustrates another embodiment of the RF amplifier 328, which includes an inductor-capacitor-inductor (LCL) filter/resonator 334 including first and second inductors 334a and 334b with a capacitor 334c disposed therebetween interconnecting the leads 227a and 227b. The LCL filter 334 transforms the voltage source of the converter/inverter output into a current source as seen from the terminals of the load.

Figure 13:
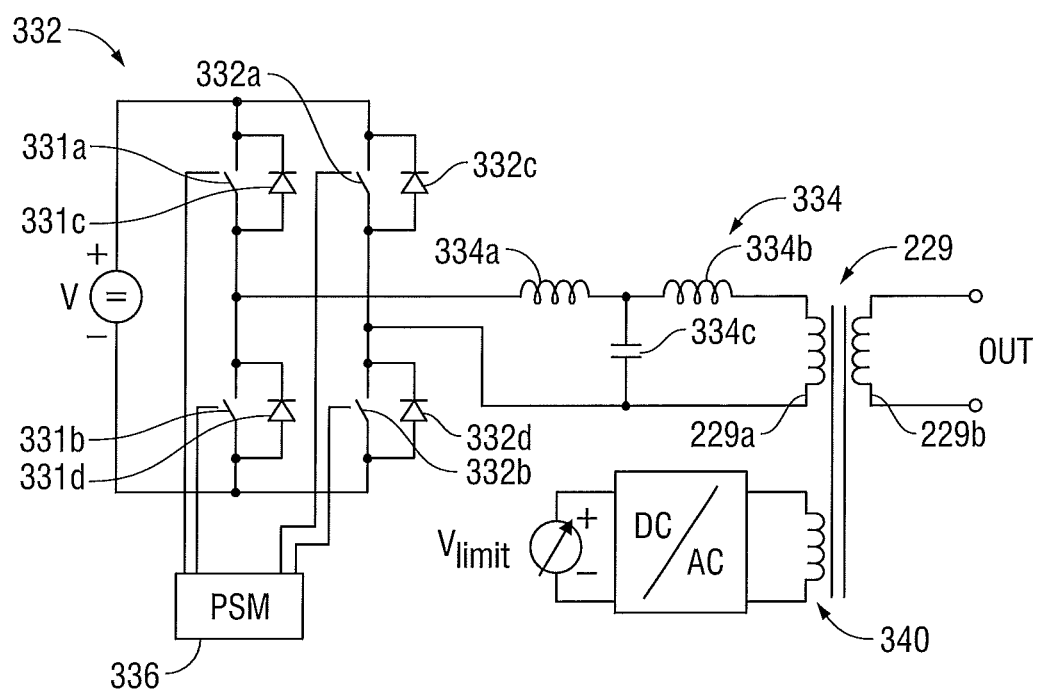
FIG. 13 is a schematic diagram of an RF amplifier of the generator of FIG. 2 according to an embodiment of the present disclosure.

With reference to FIG. 13, another embodiment of the inverter 332 is shown. The inverter 332 is configured as a phase-shifted, synchronous, full-bridge inverter including four switching elements 331a, 331b, 332a, 332b clamped with diodes 331c, 331d, 332c, 332d, respectively. Each of the switching elements 331a, 331b, 332a, 332b is controlled by the PWM 336 that may be a phase-shifted modulator similar to that described in U.S. Patent Publication 2006/0161148. The PWM 336 modulates the current amplitude of the output of the inverter 332 observed at the output terminals of the transformer secondary winding 229b. The output of the inverter 332 is coupled to the transformer 229 having a primary winding 229a and a secondary winding 229b. In addition, the inverter 332 includes an active clamp 340. The active voltage clamp 340 is coupled to a primary winding 229a of the transformer 229 along with the output of the filter 334 thereby clamping the output voltage seen at the output terminals of the transformer secondary winding 229b. The secondary winding 229b is coupled to the connectors 250, 252, 254, 256, 258, 260, 262 of the generator 200.

Figure 14:
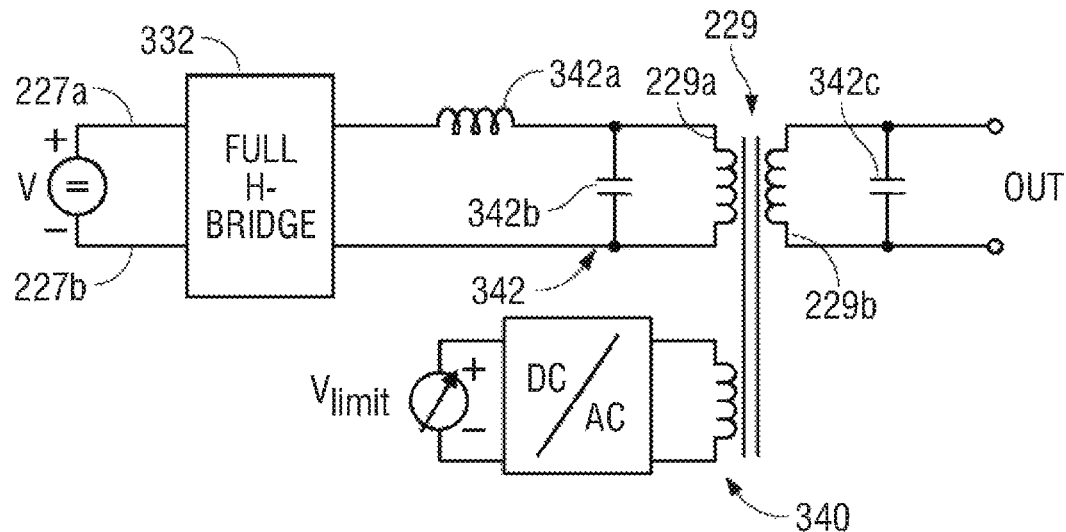
FIG. 14 is a schematic diagram of an RF amplifier of the generator of FIG. 2 according to an embodiment of the present disclosure.

FIG. 14 shows another embodiment of the inverter 332 having an LC-C filter 342 having a inductor 342a disposed on the lead 227a and a capacitor 342b interconnecting the leads 227a and 227b, forming a first portion of the LC filter 342 that is coupled to the primary winding 229a of the transformer 229. A second capacitor 342c interconnects two leads of the secondary winding 229b of the transformer 229.

Figure 15:
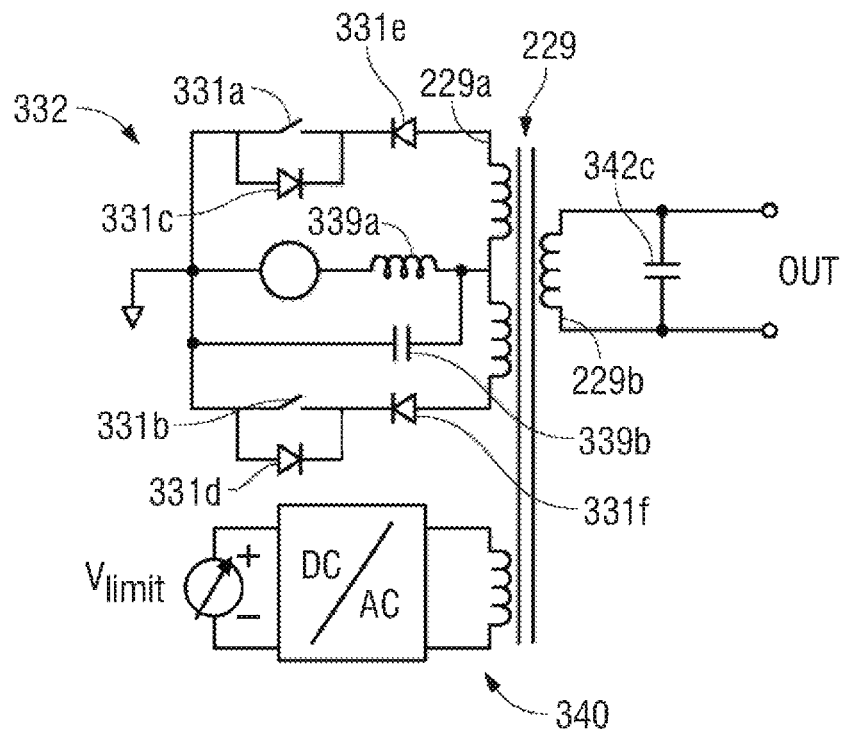
FIG. 15 is a schematic diagram of an RF amplifier of the generator of FIG. 2 according to an embodiment of the present disclosure.

FIG. 15 shows the inverter 332 that is configured as a phase-shifted, synchronous, half-bridge inverter including switching elements 331a and 331b clamped (e.g., connected in parallel) with diodes 331c and 331d, respectively, and reverse-biased diodes 331e and 331f coupled in series with the switching elements 331a and 331b, respectively. The inverter 332 also includes an LC filter 339 having an inductor 339a and a capacitor 339b connected in parallel thereto. The PWM 336 also modulates the current amplitude of the output of the inverter 332 and the output of the inverter 332 is coupled to the transformer 229 as described above. In addition, the inverter 332 includes the active clamp 340 that is coupled to a primary winding 229a of the transformer 229 along with the output of the filter 339.

Figure 16:
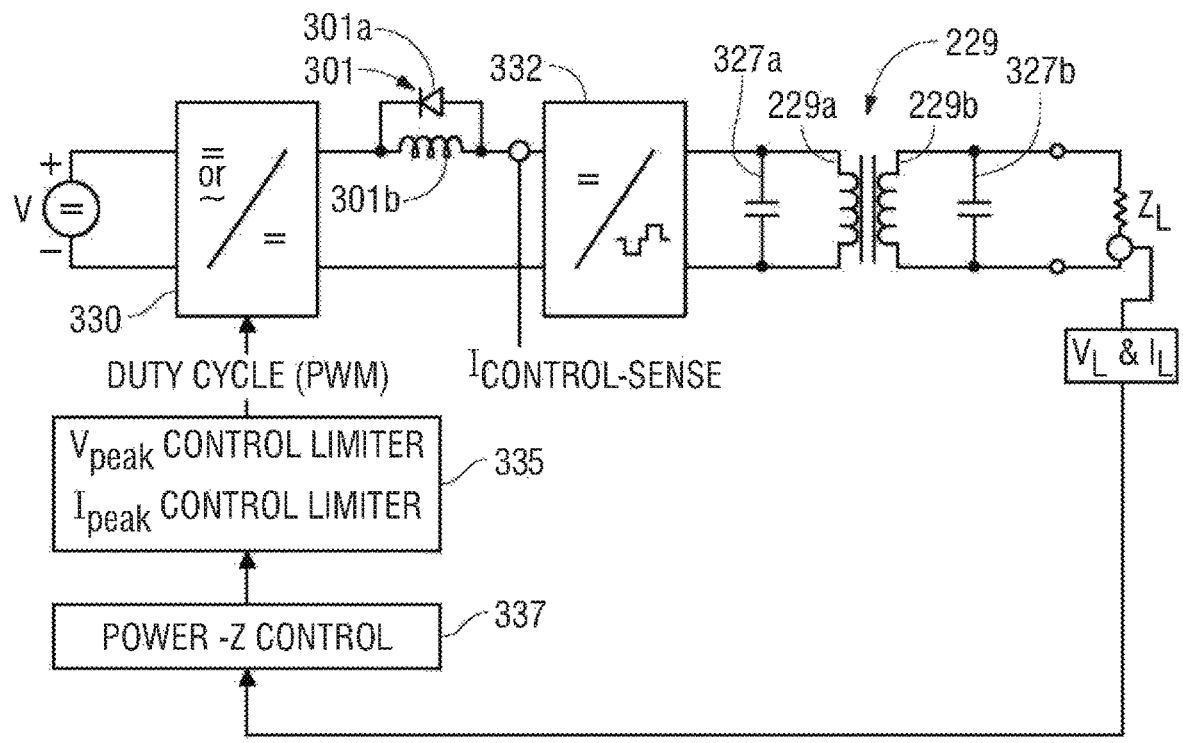
FIG. 16 is a schematic diagram of an RF amplifier of the generator of FIG. 2 according to an embodiment of the present disclosure.

FIG. 16 shows another embodiment of the RF amplifier 328 including the converter 330, the inverter 332 and the voltage limiting circuit 301 disposed therebetween. The RF amplifier 328 further includes the voltage limiter 335 and a power/impedance control 337, which may be implemented as software algorithms within the controller 224. The voltage limiter 335 and the power/impedance control 337 receive feedback from the primary winding 229a and the secondary winding 229b of the transformer 229, respectively. The RF amplifier 328 further includes a first capacitor 327a and a second capacitor 327b disposed on the primary winding 229a and the secondary winding 229b of the transformer 229, respectively. The capacitors 327a and 327b are configured to resonate with the primary winding 229a to provide for sinusoidal output of the RF amplifier 328.

The RF amplifiers 328 of FIGS. 10-16 are configured to output mean constant power in the presence of arcing. In one embodiment, the inverter 332 may be operated using a constant current power control loop by limiting duty cycle maximums of the PWM signal supplied to the switching elements using the PWM 336. The control loop may be implemented using the PID controller 338. In embodiments, where the voltage and current limits do not correspond to the power curve, the constant power control loop may be implemented by limiting the maximum duty cycle in response to measured impedance.

Figure 17:
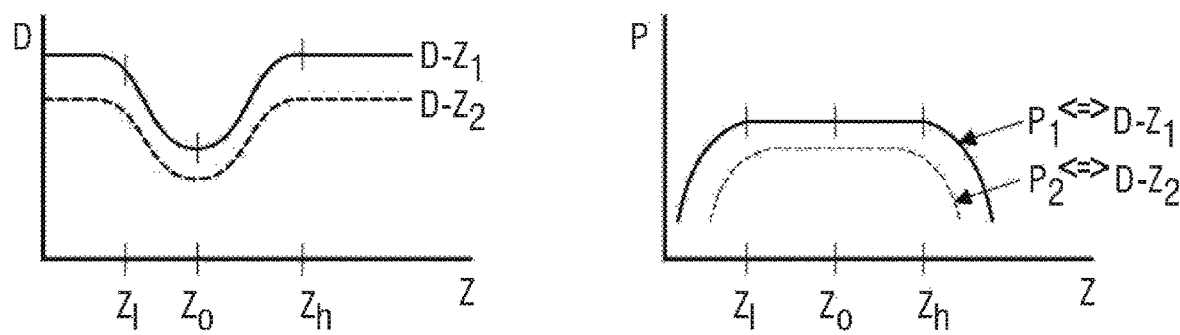
FIG. 17 illustrates duty cycle and power as a function of impedance plots for controlling output of the generator of FIG. 2 according to an embodiment of the present disclosure.

In further embodiments, a duty cycle as a function of impedance curve may be used as shown in FIG. 17. The duty cycle vs. impedance curve provides constant power, voltage, and/or current control for any measured impedance value as illustrated by a duty cycle plot 600 and a constant power plot 602 extrapolated therefrom. The plot 602 or constant current and constant voltage plots may be linearized to the plot 600 to match the control curves. In further embodiments, other transfer functions may be used to map the relationship between impedance and power with respect to duty cycle control. The duty cycle plot 600 may be implemented as a look-up table and/or software executable by the controller 224 thereby allowing for control of the duty cycle for an input value of the measured impedance. In embodiments, the PID controller 338 may control the output of the generator 200 by adjusting the duty cycle based on measured impedance to achieve desired discharge characteristics.

In embodiments in which the electrosurgical waveform is pulsatile, upon detecting arc discharges, the generator 200 may increase the time between pulses of the electrosurgical waveform (e.g., lower the duty cycle) to allow the electrode 3 to cool. In another embodiment, the generator 200 may reduce the current to prevent the electrode 3 from overheating. Conversely, shortening the time between pulses may be used to insure that arcs are generated when arcing is desired (e.g., cutting). The adjustments to the generator 200 may be embodied in either hardware and/or software to be performed automatically or in response to user input (e.g., entering pulse delay). In a further embodiment, the generator 200 is configured to detect a resistive contact between the electrode 3 and the tissue (e.g., 0 V simultaneous with 0 A) and increase power and/or voltage to initiate arc discharges or lower power or voltage to extinguish arc discharges.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling an electrosurgical generator, the method comprising:
    generating an electrosurgical waveform through an RF output stage comprising a pulse-width-modulator coupled to an RF inverter and a resonant matching network coupled to the RF inverter, which is coupled to a winding of a transformer and a power source configured to output DC current, wherein voltage-current characteristics of the RF output stage define an ellipse centered at a mean of minimum and maximum terminating resistances;
    applying the electrosurgical waveform to tissue through an electrode, the electrosurgical waveform including a plurality of cycles;
    measuring a voltage and a current of the electrosurgical waveform;
    determining a voltage limit or a current limit based on a voltage limit and a current limit inherent to voltage-current characteristics of the RF output stage;
    supplying a control signal to the pulse-width-modulator based on the voltage limit or the current limit to saturate the RF output stage based on voltage-current characteristics of the RF output stage; and
    clamping voltage of the electrosurgical waveform through an active voltage clamp coupled to the winding of the transformer, such that an output of the active voltage clamp is transmitted directly to the winding of the transformer.

2. The method according to claim 1, wherein the RF output stage comprises a switching element coupled to a controller.

3. The method according to claim 2, wherein the controller comprises a proportional-integral-derivative controller and the pulse-width-modulator, wherein pulse-width-modulator is configured to output the control signal to the switching element and adjust a duty cycle of the control signal based on an output of the proportional-integral-derivative controller.

4. The method according to claim 3, wherein the controller is configured to determine impedance based on the measured voltage and current.

5. The method according to claim 4, wherein the proportional-integral-derivative controller is configured to provide the output based on the impedance.

6. The method according to claim 3, wherein the proportional-integral-derivative controller comprises a voltage limiter function.

7. The method according to claim 4, wherein the proportional-integral-derivative controller comprises a current limiter function.

8. The method according to claim 1, further comprising:
generating DC current at a power supply coupled to the RF output stage; and
supplying the control signal to the power supply based on the voltage limit or the current limit to saturate the RF output stage based on the voltage-current characteristics of the RF output stage.

* * * * *